United States Patent [19]
Aznoian et al.

[11] Patent Number: 6,083,150
[45] Date of Patent: Jul. 4, 2000

[54] ENDOSCOPIC MULTIPLE SAMPLE BIOPSY FORCEPS

[75] Inventors: Harold M. Aznoian, North Andover, Mass.; Frank V Patterson, Exeter, N.H.; Peter J. Lukin, Lancaster; John E. Dimitriou, Stow, both of Mass.; Steven L. Lantagne, Salem, N.H.; Edward C. Page, Baldwinville, Mass.

[73] Assignee: C. R. Bard, Inc., Billerica, Mass.

[21] Appl. No.: 09/268,138

[22] Filed: Mar. 12, 1999

[51] Int. Cl.⁷ .................................................. A61B 10/00
[52] U.S. Cl. ........................................ 600/56 F; 606/205
[58] Field of Search .................................... 600/562, 564, 600/567; 606/205, 206, 207, 208

[56] References Cited

U.S. PATENT DOCUMENTS

| | | | |
|---|---|---|---|
| 3,729,008 | 4/1973 | Berkovits | 128/418 |
| 4,176,662 | 12/1979 | Frazer | 128/6 |
| 4,509,517 | 4/1985 | Zibelin | 128/319 |
| 4,887,612 | 12/1989 | Esser et al. | 128/751 |
| 4,958,642 | 9/1990 | Christian et al. | 128/772 |
| 5,052,402 | 10/1991 | Bencini et al. | 128/751 |
| 5,147,378 | 9/1992 | Markham | 606/206 |
| 5,172,700 | 12/1992 | Bencini et al. | 128/751 |
| 5,318,589 | 6/1994 | Lichtman | 606/205 |
| 5,383,471 | 1/1995 | Funnell | 128/751 |
| 5,496,317 | 3/1996 | Goble et al. | 606/48 |
| 5,522,830 | 6/1996 | Aranyi | 606/174 |
| 5,535,754 | 7/1996 | Doherty | 128/751 |
| 5,542,432 | 8/1996 | Slater et al. | 128/751 |
| 5,569,298 | 10/1996 | Schnell | 606/205 |
| 5,611,813 | 3/1997 | Lichtman | 606/205 |
| 5,636,639 | 6/1997 | Turturro et al. | 128/751 |
| 5,638,827 | 6/1997 | Palmer et al. | 128/751 |
| 5,645,075 | 7/1997 | Palmer et al. | 128/749 |
| 5,762,069 | 6/1998 | Kelleher et al. | 128/751 |
| 5,776,075 | 7/1998 | Palmer | 600/564 |
| 5,779,648 | 7/1998 | Banik et al. | 600/567 |

FOREIGN PATENT DOCUMENTS

| | | | |
|---|---|---|---|
| 2 479 680 | 10/1981 | France | A61B 10/00 |
| WO 95/08946 | 4/1995 | WIPO . | |

OTHER PUBLICATIONS

Lewis, J., "Steerable forceps make sinus surgery easier" Design News, Jun. 8, 1998, p125–126.

*Primary Examiner*—Max Hindenburg
*Assistant Examiner*—Paula Wingood
*Attorney, Agent, or Firm*—Darby & Darby

[57] ABSTRACT

A endoscopic multiple sample biopsy forceps is disclosed having a jaw assembly with a pair of jaws connected to a pair of arms extending from a jaw housing. Each jaw has two shanks oppositely displaced from the longitudinal axis of the device to define a space in the rear of the jaw for storing collected tissue samples. The tissue storage space defined by the jaw shanks opens rearwardly into a tissue storage area defined within the housing. Each shank has a broad outwardly facing planar surface aligned with an inwardly facing planar surface on one of the pair of arms. A cam slot on each jaw shank is slidably engaged by a cam pin on one of the pair of arms. A puller member coaxially positioned in the housing and axially movable relative to the housing supports a pair of pivots, each of which pivotally engages a bore on at least one jaw shank. The puller member is attached to a drive wire coaxially positioned in a tubular shaft. Axial movement of the drive wire actuates the puller member. In response to axial movement of the puller along the longitudinal axis of the outer tube, the cam pins riding in the cam guide slots change the position relative to the fixed jaw pivot axis of the jaw, thus actuating the jaws. None of the jaw assembly elements movable relative to the device, except the jaws, are externally exposed such that they could contact targeted tissue and negatively affect tissue sampling operations. An ejector is provided to push collected samples from the tissue sample storage area.

11 Claims, 8 Drawing Sheets

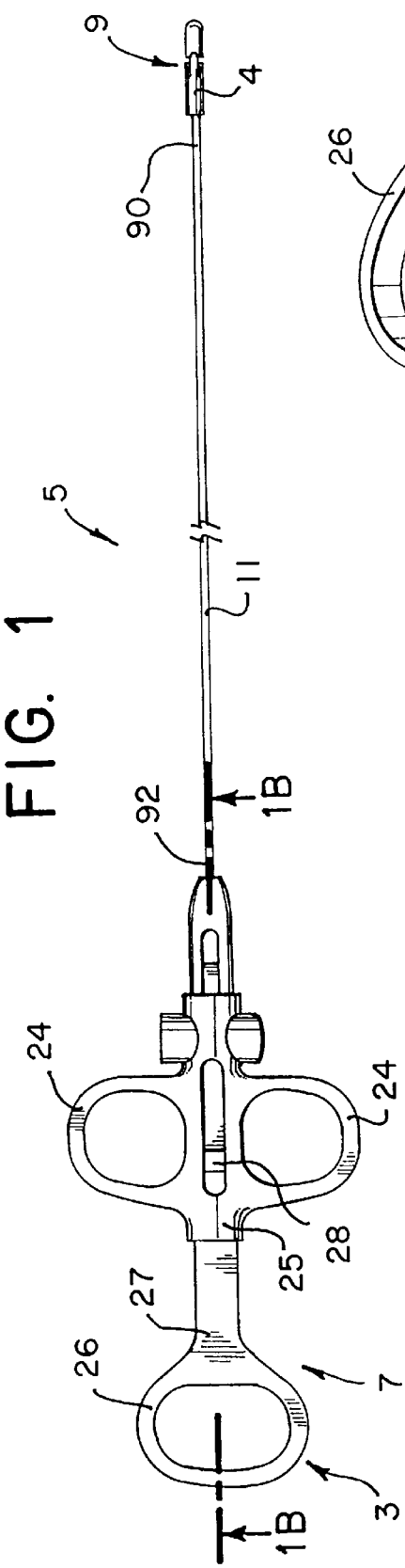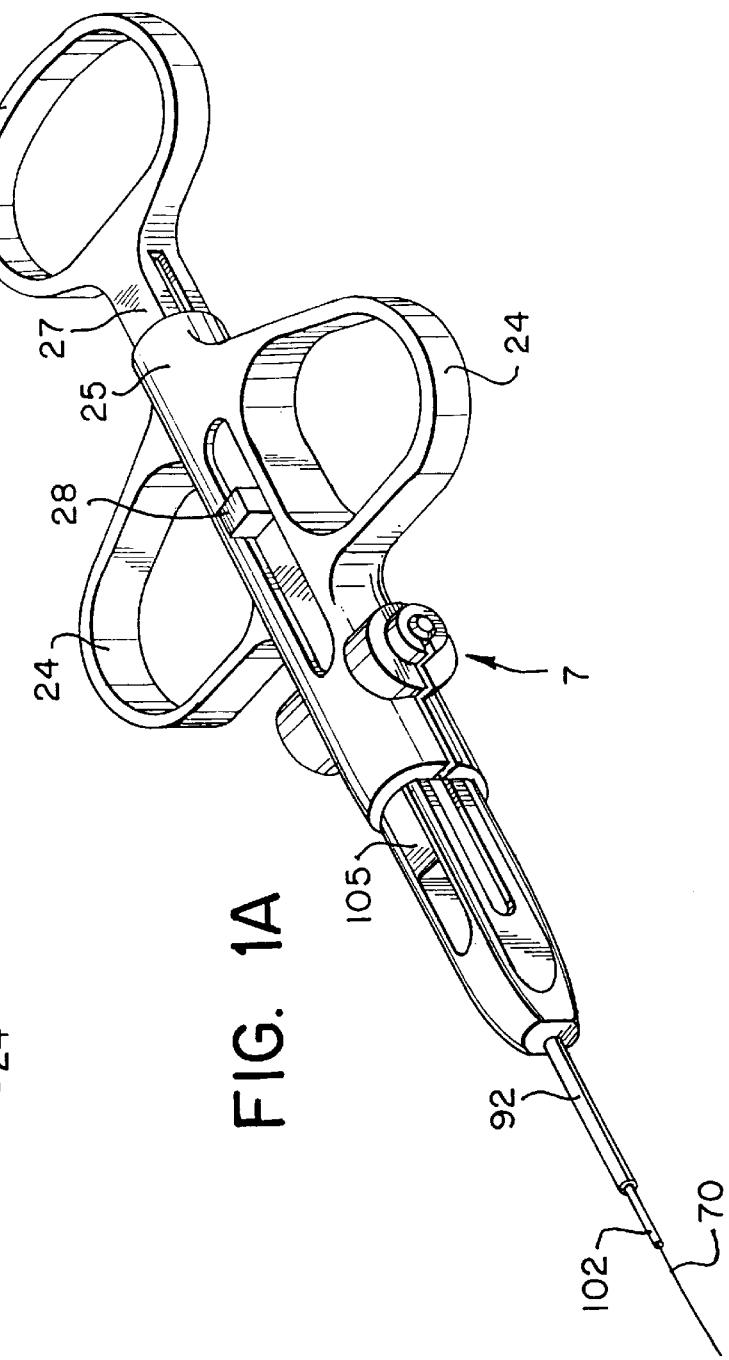

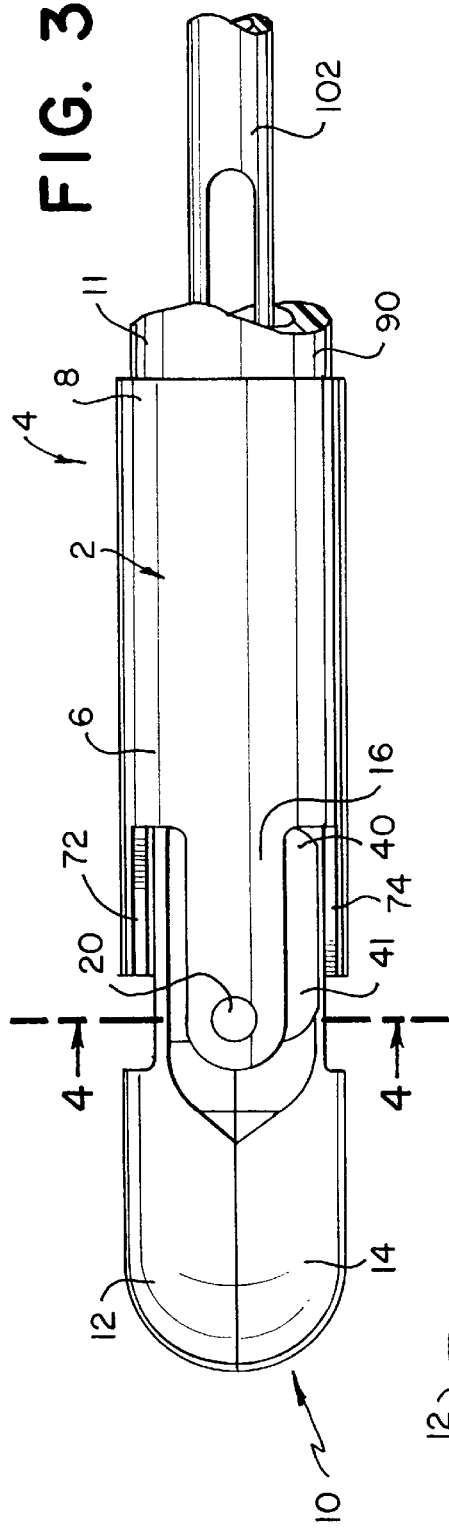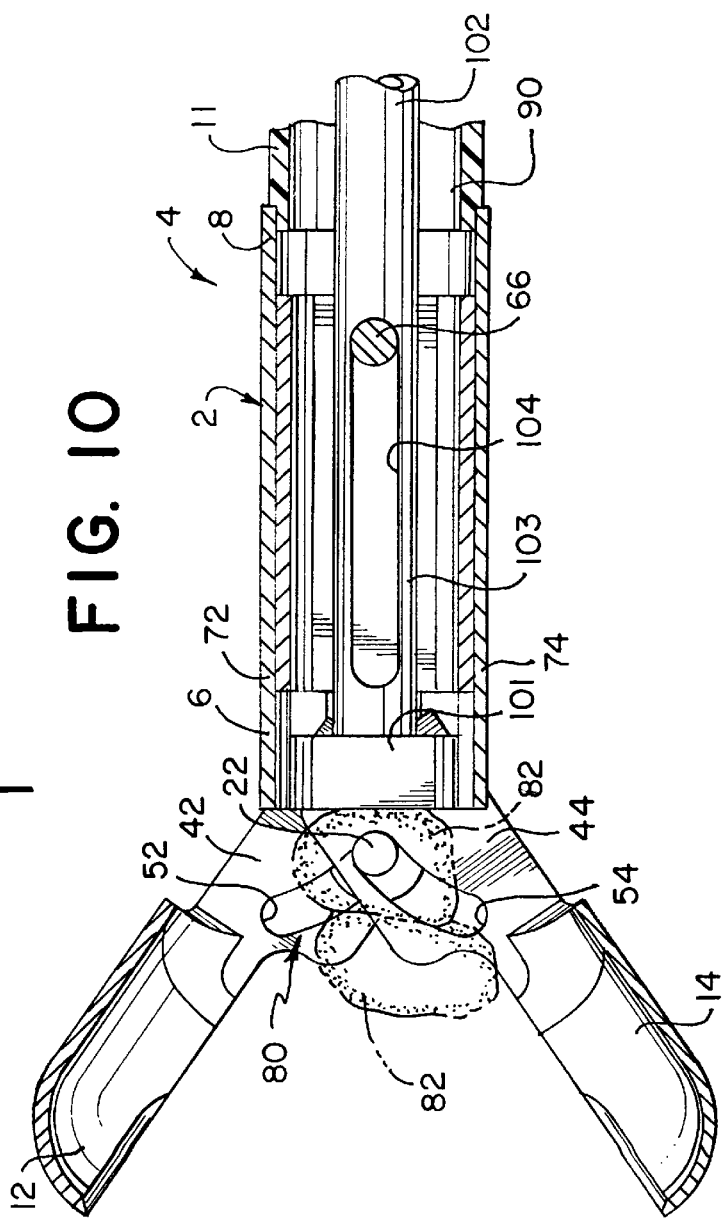

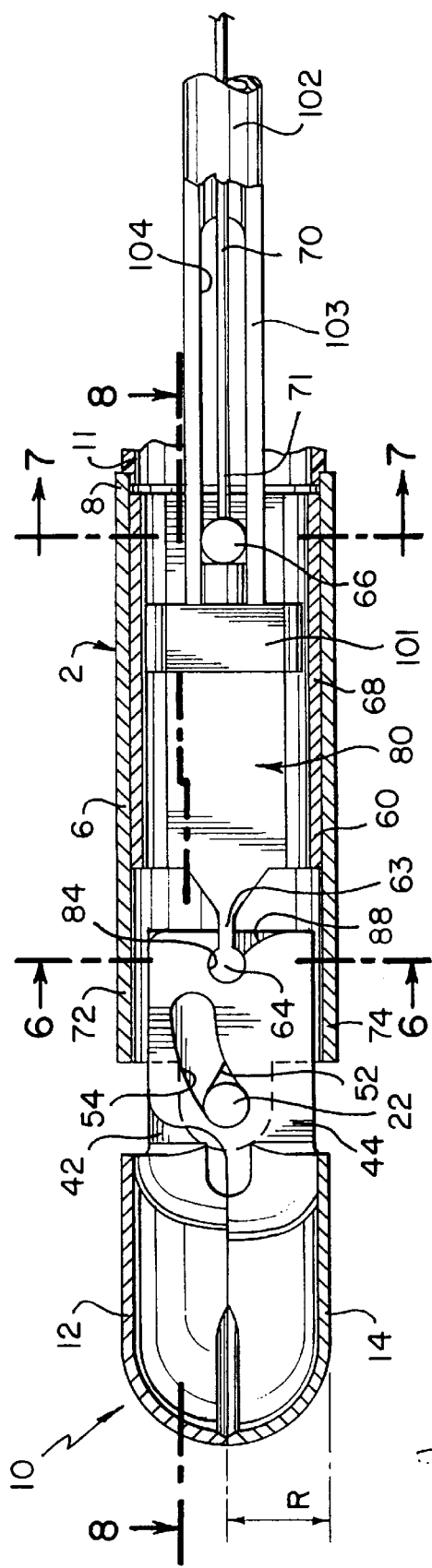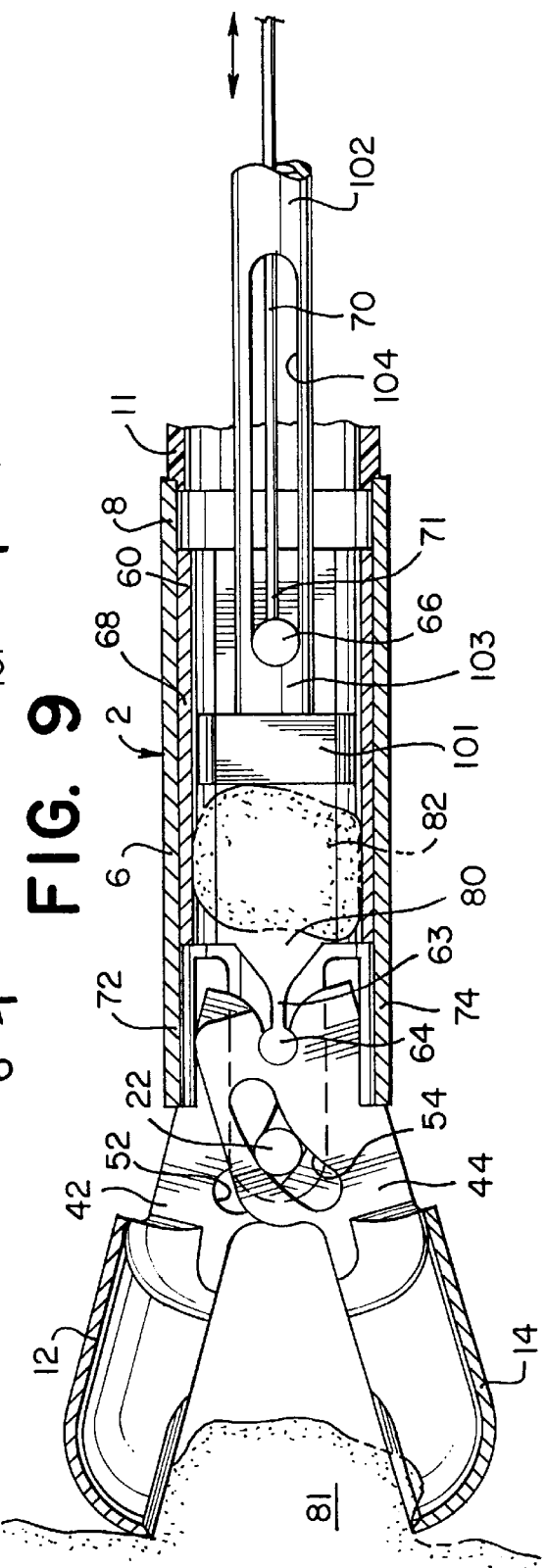

ENDOSCOPIC MULTIPLE SAMPLE BIOPSY FORCEPS

BACKGROUND OF THE INVENTION

1. Field of the Invention

The present invention relates generally to endoscopic forceps capable of obtaining tissue samples from a body cavity, and more particularly to endoscopic biopsy forceps with a jaw assembly capable of obtaining multiple biopsy tissue samples from a body cavity without being withdrawn from the body cavity.

2. Description of Related Art

In the diagnosis and treatment of certain illnesses, it is sometimes desirable to obtain tissue samples from deep within a body cavity, such as, for example, the large intestines of the gastrointestinal tract. In retrieving tissue samples, minimally invasive methods and devices are preferred. Endoscopic devices having dimensions which permit insertion through an endoscope, and which are capable of traversing a tortuous path through a body cavity such as the intestines, are preferred. These devices are capable of retrieving tissue samples from within a body cavity with minimal risk and/or discomfort to the patient.

An example of such a device is shown in U.S. Pat. No. 4,887,612 to Esser et al. Esser et al. disclose an elongated flexible tubular shaft with an operating handle at one end and a jaw assembly with a pair of jaws at the other end. Each jaw has a cup like end, for receiving a tissue sample, provided on the end of a jaw shank attached by a pivot to a housing, which is in turn attached to the shaft. The jaw shank of each jaw is also provided with a cam slot, in which a cam pin rides. The cam pin is connected to one end of a drive wire coaxially positioned in the tubular shaft. The other end of the drive wire is connected to the handle such that the jaw is openable and closeable in response to movement of the drive wire relative to the shaft. However, the jaw shank, pivot, pin, drive wire and jaw assembly housing structure occupy substantially all of the space immediately behind the jaw cups. Thus, the jaw assembly is only capable of receiving one tissue sample. The shaft and jaw assembly must be withdrawn from the body organ to retrieve the single sample.

In order to properly diagnose a condition or illness, it is often desirable to retrieve multiple tissue samples from a single body cavity. A device that only retrieves a single sample with each insertion must be repeatedly withdrawn and reinserted to obtain multiple samples. This is inconvenient and time consuming for the practitioner, and increases the period to which the patient is subjected to the procedure which correspondingly increases the risks associated with the procedure.

Accordingly, tissue sampling devices are desirable which are capable of retrieving multiple tissue samples from a body cavity without withdrawing the device from the body cavity.

In use, a biopsy device obtains a sample from a targeted tissue mass by closing the jaws of the device to cut or tear a tissue sample from a targeted mass. Examples of targeted tissue mass include a cavity wall, a polyp, etc. Ideally, the relative position of the jaw assembly of a biopsy device should remain fixed with respect to the tissue being sampled, so that the tissue sample size, source and quality can be selectively controlled. Thus, it is preferable to have a device that permits the jaw assembly to remain stationary relative to the targeted tissue, or a device which avoids moving the targeted tissue relative to the jaw assembly during the actual taking of the tissue sample. To achieve this end, it is desirable in the design of tissue sampling devices to provide that portion of the device which is inserted into the cavity, i.e., the distal end, with as few externally exposed moving parts as possible, particularly jaw assembly parts close to the distal end of the jaw assembly. The externally exposed parts referred to are those parts, other than the jaws, which are exposed externally of the device such that the parts could contact and move the targeted tissue or tissue immediately adjacent to targeted tissue during the taking of a tissue sample. The movement referred to is movement of jaw assembly elements relative to the device shaft, relative to the distal end of the jaw assembly, or relative to the tissue being sampled. By eliminating externally exposed moving parts, undesired tissue movement can be avoided. Examples of externally exposed moving parts include, but are not limited to, the tubular shaft of an endoscopic device if it moves axially or radially relative to the jaws, as for example in a device in which the jaw assembly is stationary relative to an inner drive wire, and the outer tubular shaft is movable relative to the inner wire to, for example, open and close the jaws. Further examples of externally exposed moving parts include, but are not limited to, jaw assembly parts such as housing members or jaw actuating members, sleeves or arms. These types of moving parts are known to contact and transmit movement either directly to targeted tissue, or indirectly to targeted tissue by contacting tissue adjacent to targeted tissue, thus reducing the accuracy of the sampling procedure as well as the quantity and quality of the tissue samples retrieved.

A device capable of retrieving multiple tissue samples is disclosed in U.S. Pat. No. 5,318,589 to Lichtman. Lichtman discloses jaws mounted on an inner member, a movable intermediate member extendable over the jaws to close the jaws, and an outer sleeve which occupies substantially the entire length of the intermediate shaft. The inner member and outer sleeve are stationary relative to the jaws. The outer sleeve prevents movements of the intermediate shaft from being transmitted to the targeted or surrounding tissue. The arrangement taught by Lichtman has the disadvantage of requiring a third coaxial member, i.e., the stationary inner member, which occupies space in the jaw assembly that could otherwise be occupied by tissue samples, thus limiting the number of samples that can be retrieved without withdrawing the distal end from the body cavity.

U.S. Pat. No. 5,542,432 to Slater et al. discloses a biopsy forceps device capable of retrieving multiple tissue samples. The device has a pair of jaw cups, each on a thin resilient arm connected to an elongate tubular shaft such that they are axially stationary relative to the tubular shaft, i.e. stationary relative to the targeted tissue. A cylinder connected to an inner control wire extends over the resilient arms to close the jaws. Each additional tissue sample taken pushes the previous sample further back into the jaw assembly, between the thin resilient arms. The disadvantage of this arrangement is that the cylinder may be externally exposed to contact and transmit movement to targeted tissue, thus affecting the quality and quantity of samples retrieved. The arrangement has an additional disadvantage in that the thin resilient arms lack means to laterally contain collected samples, thus tissue samples are likely to be lost to retrieval by being pushed or jarred from the storage area between the thin resilient arms. Finally, this arrangement suffers yet another disadvantage in that the thin resilient arms permit the jaws to move laterally out of alignment with each other, such that the quality and/or quantity of a tissue sample may be diminished.

There is therefore a need for an endoscopic biopsy device capable of taking multiple biopsy samples without being withdrawn from a body cavity, the device having a jaw assembly with few or no externally exposed moving parts (except the jaws) and having a relatively large and contained storage area for collecting multiple samples.

SUMMARY OF THE INVENTION

A multi-sample biopsy forceps device is disclosed having a jaw assembly with a pair of jaws connected to a tube-like jaw housing, also referred to as an outer tube. The pair of jaws are opened and closed in response to axial movement of a sleeve-like actuator, referred to herein as a puller member. The sleeve-like actuator or puller member is arranged coaxially within the jaw housing. Each of the jaws has a cup-like forward biting portion, and at least one shank extending towards the jaw housing. Each jaw shank defines an outwardly directed planar surface which is aligned with a corresponding inwardly directed planar surface on an arm extending from the jaw housing toward the jaw cups. Each jaw shank is also laterally offset from a longitudinal axis of the biopsy device to form an open rear end of the jaw. The rear end of each jaw opens into the jaw housing. The rear end of each jaw defined by the laterally offset jaw shank also defines a storage portion in the jaw, which in turn defines at least part of a tissue sample storage area in the jaw assembly. When the at least one jaw shank of each jaw is positioned on an opposite side of the jaw assembly from the other jaw shank, the jaw shanks laterally contain the portion of the storage area between the jaws to prevent the lost of stored samples. The rear of each jaw opens into the jaw housing such that the jaw assembly tissue sample storage area may extend rearwardly from the rear end of the jaws into a portion of the jaw housing. The jaw housing is fixed to an elongate flexible tubular shaft. The puller member is located inside the housing and is connected to the proximal end of the shank of each jaw. The pair of jaws are connected to the housing by cam means comprising at least one cam slot on each jaw shank angled in a direction opposite that of a cam slot on the shank of the other jaw, with at least one common cam pin extending from the jaw housing to slidably engage the cam slots. The cam pin thus engages two oppositely angled cam slots. Preferably both jaws are pivotable about a common pivot axis on one or more pivot pins.

Preferably, the puller member has planar surfaces corresponding to the planar surfaces of the shank or shanks of each jaw. In response to movement of the puller member along the longitudinal axis of the tubular shaft, each jaw shank is displaced relative to the jaw housing, causing the cam pins riding in the cam guide slots to change position relative to the fixed jaw pivot axis of the jaw, thus actuating the jaw. The foregoing arrangement provides several advantages. The rearwardly open ended sample storage portion of the jaws permits the collection and secure retention of multiple tissue samples. The housing, and the jaws mounted to the housing, can be held stationary relative to the flexible tubular shaft, and thus, relative to the sampling site, so that tissue sampling is more precise and better samples can be obtained, e.g., the jaws do not "pull away" from a sample site when closed. Since the puller member is inside the outer tube, it actuates the jaws without disturbing surrounding tissue, thus enhancing tissue sampling precision. Because it is coaxially aligned with the rear end of the pair of jaws, the puller member provides a jaw actuating mechanism that occupies minimum space, thus freeing space within the jaw assembly for collecting multiple samples. The puller member acting together with the jaw cam pins and inclined cam slots provided on the jaw shanks wider than the jaw cup provides significant mechanical advantage in actuating the jaws for taking tissue samples.

BRIEF DESCRIPTION OF THE DRAWINGS

The foregoing and other objects and advantages of the invention will be appreciated more fully from the following further description thereof, with reference to the accompanying drawings wherein:

FIG. 1 is a top plan view of the multiple sample biopsy device with a portion of the flexible shaft omitted for brevity, as indicated by the gap in the shaft;

FIG. 1A is a perspective view of the handle assembly depicted in FIG. 1;

FIG. 3 is a side elevational view of the jaw assembly depicted in FIGS. 1 and 2;

FIG. 5 is a sectional view from the side of the jaw assembly depicted in FIGS. 1, 2, 3 and 4, taken along line 5—5 in FIG. 4, showing the pair of jaws closed and the ejector in its proximal position;

FIG. 9 is a sectional view from the side of the jaw assembly depicted in FIGS. 1, 2, 3, 4, 5, 6, 7 and 8, showing the pair of jaws open to receive a tissue sample, and showing the ejector between a proximal and a distal position;

FIG. 10 is a sectional from the side of the jaw assembly depicted in FIGS. 1, 2, 3, 4, 5, 6, 7, 8 and 9, showing the pair of jaws open, and showing the ejector in a distal position pushing tissue samples from the sample storage area;

DETAILED DESCRIPTION

Figure 1B:
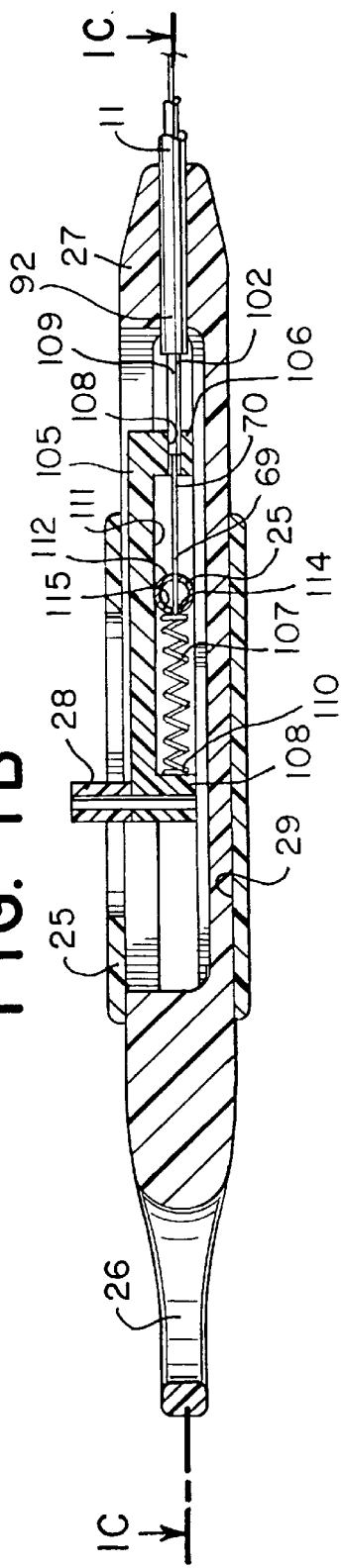
FIG. 1B is a sectional view of the handle assembly depicted in FIGS. 1 and 1A, taken along line 1B in FIG. 1.

Referring to FIG. 1, a multi-sample biopsy forceps device according to the present invention is shown generally at 5 having a proximal end 3 with a handle assembly 7, and a distal end 9 with a jaw assembly 4. An elongate flexible tubular shaft 11 having a proximal end 92 and a distal end 90 connects the handle assembly 7 to the jaw assembly 4. The tubular shaft 11 is made of materials and by methods well known in the art, e.g., a tightly coiled metal forms the body of the tube and a bio-compatible plastic sheathing is applied to the external surface of the tube. A longitudinal axis is defined from the proximal end 3 to the distal end 9 of the biopsy device 5.

Figure 1C:
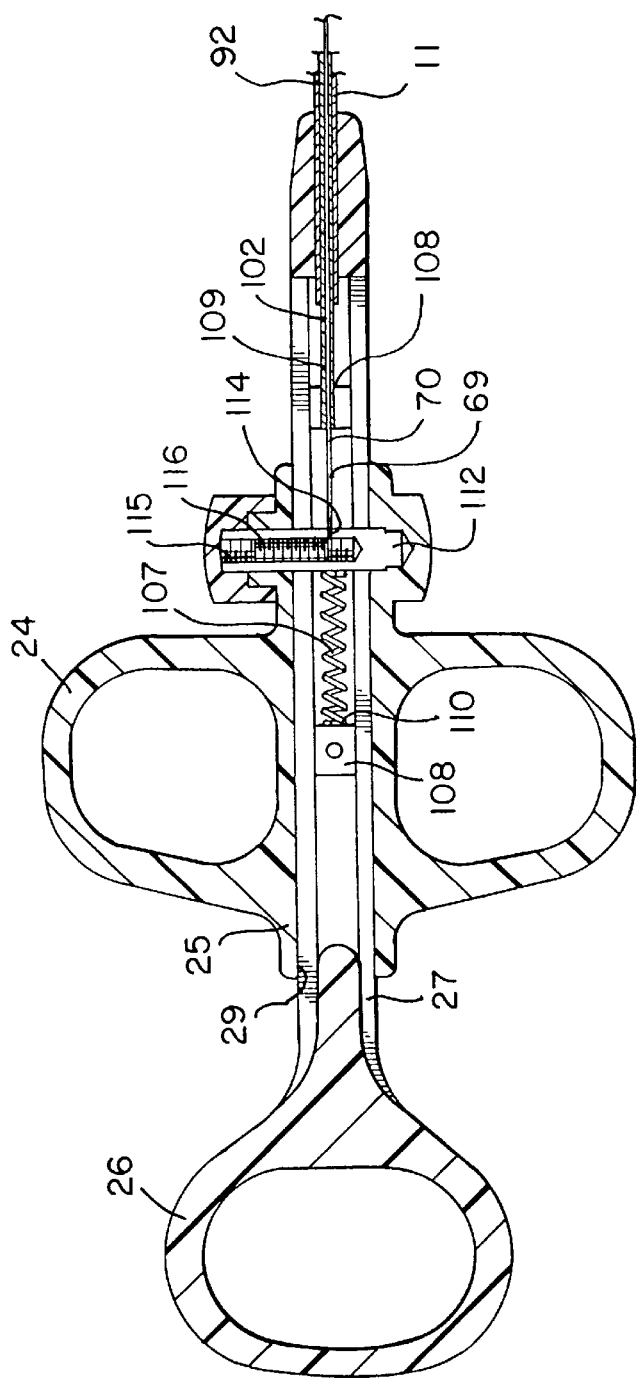
FIG. 1C is a sectional view of the handle assembly depicted in FIGS. 1, 1A and 1B, taken along line 1C in FIG. 1B.

The handle assembly 7, shown in more detail in FIGS. 1A–1C, has a thumb ring 26 integrally formed on a proximal end of a thumb support member 27. A proximal end 92 of the flexible shaft 11 is fixedly connected to the distal end of the thumb member 27, for example, by an adhesive, or by welding, swaging or other well known attachment means. A finger member 25 is supported on the thumb member 27 such that the finger member 25 is moveable on the thumb member 27 along the longitudinal axis of the biopsy device 5. A pair of finger rings 24 are integrally molded on opposite sides of the finger member 25. An ejector knob 28 is slidably supported on the thumb member 27 such that it is operable independently of the thumb member and independently of the finger members.

Figure 2:
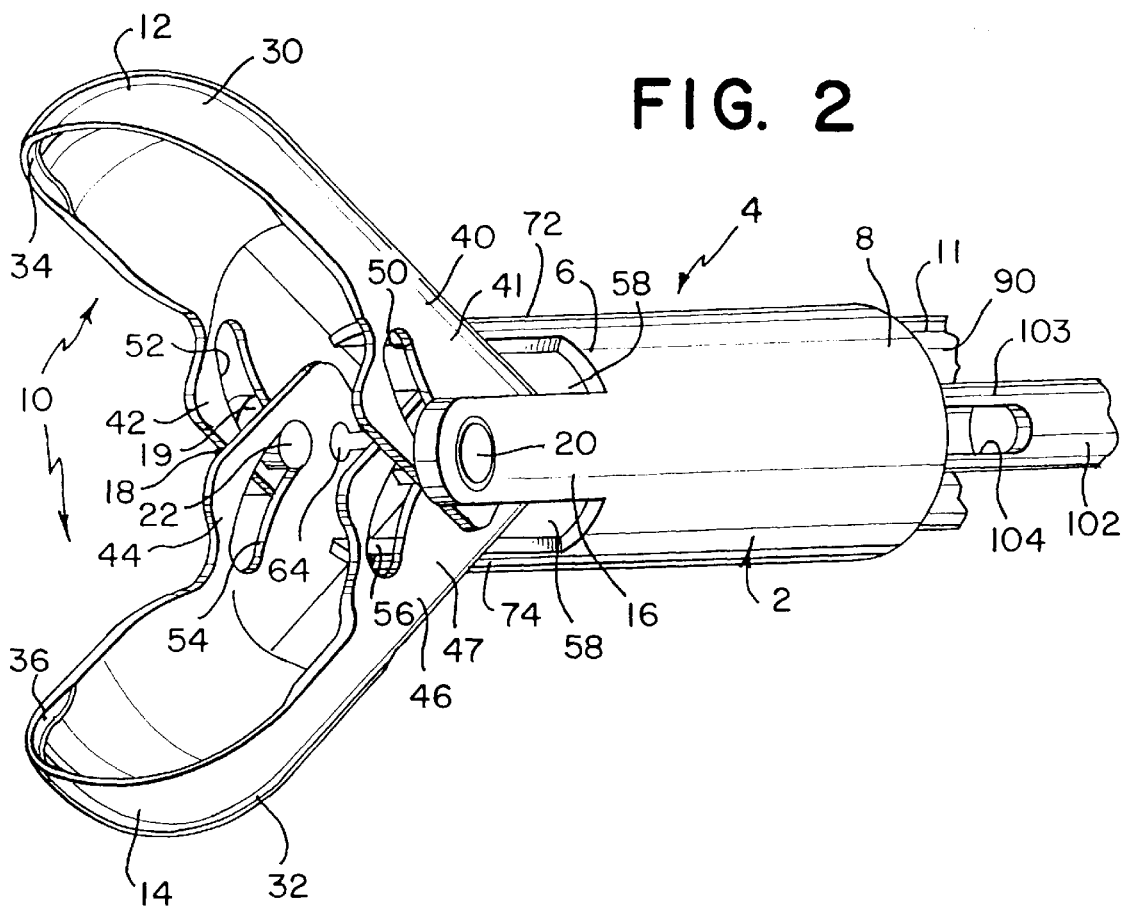
FIG. 2 is a perspective view of the preferred embodiment of the jaw assembly depicted in FIG. 1.
Figure 4:
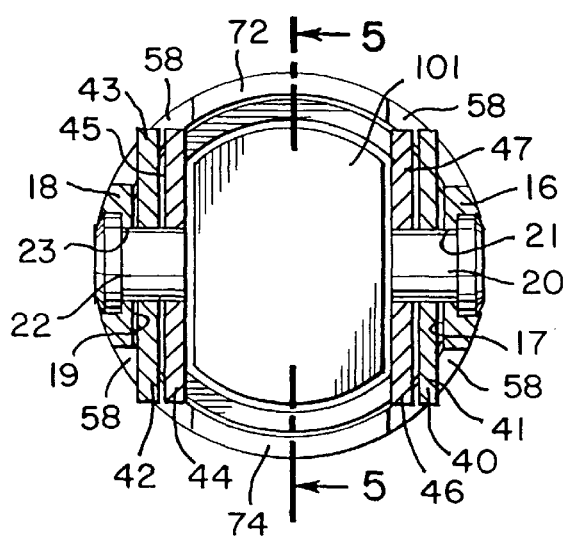
FIG. 4 is a sectional view of the jaw assembly depicted in FIGS. 1, 2 and 3, taken along line 4—4 in FIG. 3.
Figure 6:
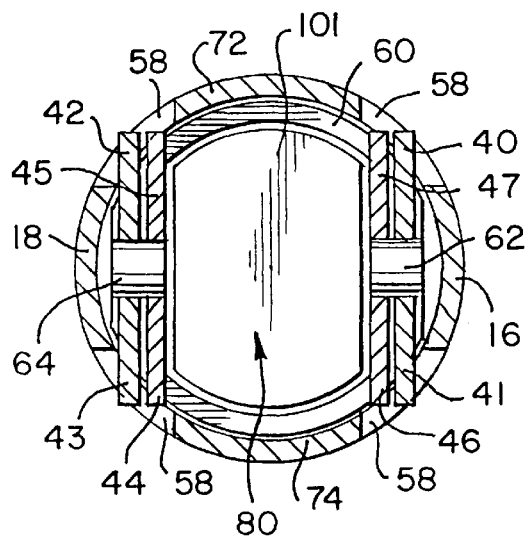
FIG. 6 is a sectional view of the jaw assembly depicted in FIGS. 1, 2, 3, 4 and 5, taken along line 6—6 in FIG. 5.

Referring to FIG. 2, the jaw assembly 4 is generally comprised of a pair of jaws 10 supported on a housing 2, a puller member 60 for actuating the jaws, and various pins and supports connecting the foregoing parts. The jaw housing 2 is tube-like, with a proximal end 8 and a distal end 6. The proximal end 8 is fixedly connected to the distal end 90 of the tubular shaft 11, by swaging, welding, adhering, or other known means. At least a first arm 16 (FIGS. 2, 3, 4 and 6) extends distally from the distal end of the housing 2 along the longitudinal axis of the biopsy device 5. Preferably a second arm 18 extends distally from an opposite side of the distal end 6 of the jaw housing 2, such that the first and second arms 16, 18 form a pair of arms to support the pair of jaws 10. The pair of jaws 10, comprising an upper jaw 12 and lower jaw 14, are mounted to the pair of arms 16 and 18. Each jaw 12, 14 has a semi-cup shaped distal end 30, 32 with a sharpened edge 34, 36 adapted for cutting tissue from a tissue mass. The dimensions of the distal end of each jaw together with the length of the sharpened edges 34, 36 along the longitudinal axis of the biopsy device define the cutting or "biting" portion of the pair of jaws. The dimensions of the biting portion of the pair of jaws substantially determines the maximum size of each tissue sample 82 taken. The dimensions of the distal end of each jaw and the length of the sharpened edges can thus be selected to facilitate the taking of samples of a particular size. The housing 2, jaws 12, 14 and other jaw assembly components are preferably made from a surgical grade of metal, but may be made of other bio-compatible materials having sufficient strength, such as, for example, plastic.

Figure 11:
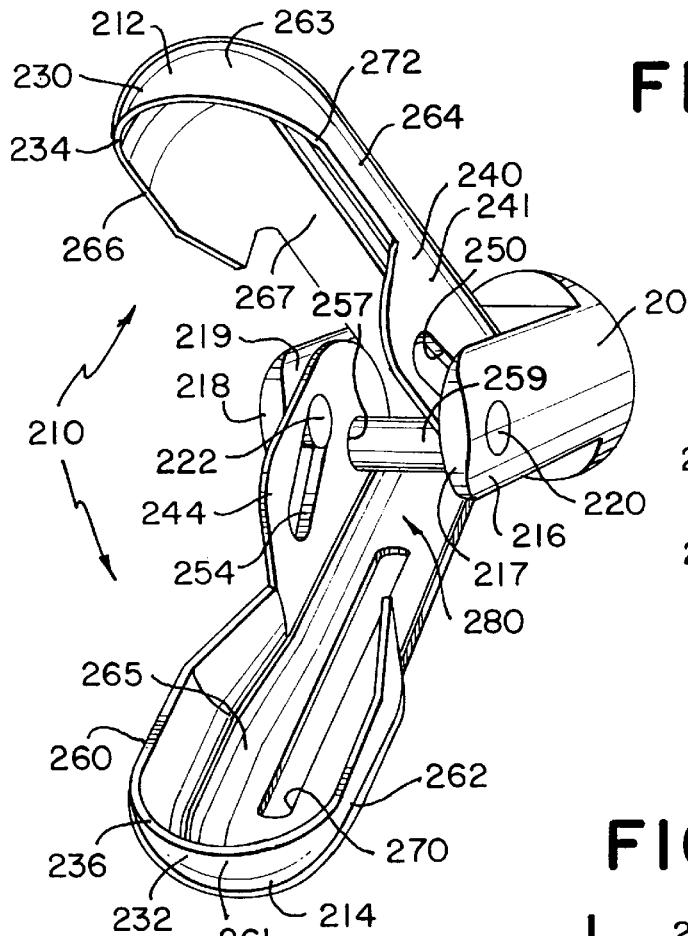
FIG. 11 is a perspective view of an alternative embodiment of the jaw assembly depicted in FIG. 1, showing the jaws in an open position.
Figure 12:
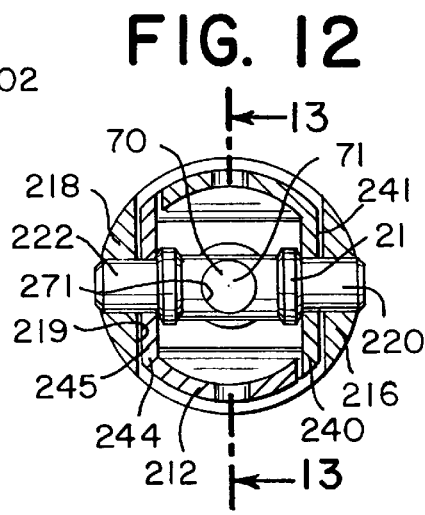
FIG. 12 is a sectional view of the jaw assembly depicted in FIG. 11 taken along line 12—12 in FIG. 13.
Figure 13:
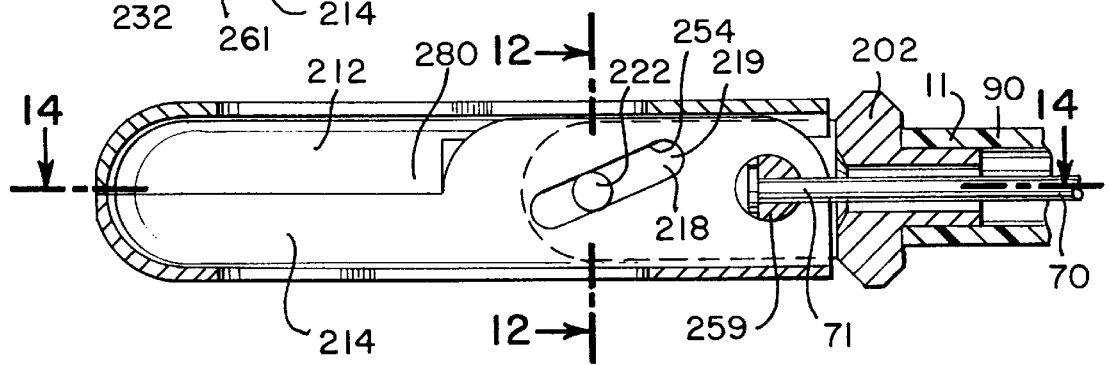
FIG. 13 is a sectional view from the side of the jaw assembly depicted in FIGS. 11 and 12.
Figure 14:
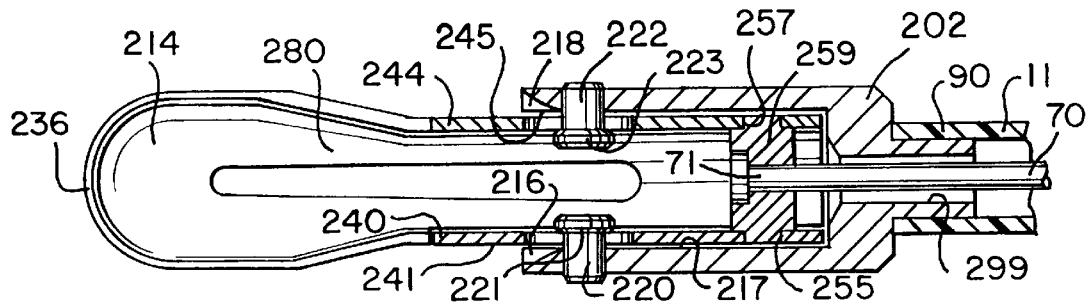
FIG. 14 is a sectional view from the top of the jaw assembly depicted in FIGS. 11, 12 and 13.

Each jaw 12, 14 also has at least a first shank 40, 44 extending from a proximal end of the jaw towards the jaw housing 2, and preferably each jaw has a second shank 42, 46 extending from an opposite side of the proximal end of the jaw towards the jaw housing 2. The first shank of each jaw preferably extends to a point between the pair of arms 16, 18. The alignment and interaction of the relatively broad planar surface of each jaw shank with the planar surfaces of at least one of the pair of arms prevents lateral twisting of the jaws away from the longitudinal axis of the device thus ensuring that the pair of jaws are always in operational alignment with the housing 2, and with each other Each shank 40, 42, 44, 46 has a length and a width defining an outwardly directed planar surface 41, 43, 45, 47, respectively, in alignment with an inwardly directed surface 17, 19 of one of the pair of arms 16, 18. Each shank 40, 42, 44, 46 is laterally offset outwardly from the longitudinal axis of the biopsy device so that the rear end of each jaw is open to receive multiple tissue samples. The first shank 40 of the upper jaw 12 and the first shank 44 of the lower jaw 14 may both be laterally offset to a first side of the longitudinal axis to be connected to the first arm 16, or the first shank 40 of the upper jaw 12 may be offset to be connected to the first arm 16 while the first shank 44 of the lower jaw 14 is offset to an opposite side of the longitudinal axis to be connected to the second arm 18 (FIG. 11). This latter embodiment will be discussed in further detail below.

As noted above, preferably upper jaw 12 has a first shank 40 and second shank 42, and lower jaw 14 has a first shank 44 and a second shank 46. The first and second shanks of each jaw are laterally offset to opposite sides of the longitudinal axis such that the respective opposite jaw shanks are adjacent to and aligned with the inwardly directed surfaces 17, 19 of the arms 16, 18 in an overlapping relationship. By laterally offsetting the first and second shanks to opposite sides of the longitudinal axis of the device, the first and second shanks of each jaw define an open rear end of each jaw and define the opposite sides of at least a portion of a tissue sample storage area 80, shown in FIGS. 5, 8, 9 and 10. In the preferred embodiment, the tissue sample storage area 80 extends from between the laterally offset jaw shanks rearwardly into the jaw housing 2. Representative tissue samples 82 are shown in broken lines in the tissue sample storage area 80 in FIGS. 9 and 10. An upper containment wall 72 and lower containment wall 74 extend from the distal end 6 of the housing 2 towards the jaw cups to define the top and bottom of the portion of the tissue sample storage area 80 which is between the laterally offset jaw shanks. In this manner, the tissue sample storage 80 area is substantially contained on all sides to prevent the loss of tissue samples 82 due to jarring or contact from lateral quarters. Thus, the tissue sample storage area comprises a space in the jaw assembly that extends from the proximal end of the puller member 60 to a point just behind the biting portion of the jaw cups. Since the volume of the biting portion of the pair of jaws substantially determines the size of each tissue sample 82, and since the tissue sample storage area has approximately five to ten times the volume of the biting portion of the pair of jaws, the tissue sample storage area 80 should store, for example, up to 10 samples of tissue. This number will of course vary with changes in the dimensions of the various jaw assembly components.

The semi-cup shaped distal end 30, 32 of each jaw 12, 14 has a semi-circular cross-section with a radius R substantially equal to that of the radius of the jaw housing 2 and the tubular shaft 11. Preferably, to provide greater mechanical advantage in opening and closing the jaws, the width of the each shank is greater than the radius R of the cross-section of the jaws. Because the resulting jaw shanks are wide relative to the cross-section of the jaw assembly, clearances 58 (FIGS. 2, 4 and 6) are provided between the upper containment wall 72 and arms 16 and 18, and between the lower containment wall 74 and arms 16 and 18. The clearances 58 provide room for the jaw shanks to pivot freely, thus permitting the jaws 12, 14 to open and close freely.

Each jaw shank 40, 42, 44, 46 has a cam slot 50, 52, 54, 56, respectively. Each cam slot 50, 52, 54, 56 is oriented at a diagonal relative to the longitudinal axis, with cam slots 50 and 52 on the upper jaw 12 being oriented along a first diagonal, and cam slots 54 and 56 on the lower jaw 14 oriented along a second diagonal opposite to that of the first diagonal. The angle of the diagonal slots relative to the longitudinal axis of the device and the length of the diagonal slots is selected to determine how far the jaws will open, the degree of effort required to open and close the jaws, and the speed at which the jaws open and close. The cam slots 50, 52, 54, 56 may also have a slight curve along the diagonal. The curve can be selected to further increase mechanical advantage, to control the rate of closing of the jaws or to minimize the effort required to open or close the jaws.

A cam pin 20 extends inwardly from arm 16 and is sized to extend through cam slot 50 in upper jaw 12 into cam slot 56 in lower jaw 14. Similarly, a cam pin 22 extends inwardly from arm 18 and is sized to extend through cam slot 52 in upper jaw 12 into cam slot 54 in lower jaw 14. Each cam pin 20 and 22 is made of a suitable biocompatible material, preferably a high strength plastic or metal, and is welded or swaged into a bore 21, 23, respectively, on arms 16, 18, respectively, such that each cam pin 20, 22 is stationary relative to the longitudinal axis of the biopsy device 5. Thus, when the jaw shanks 40, 42, 44, 46 are moved axially relative to the jaw housing 2, the cam slots 50 and 56 are drawn over cam pin 20, and the cam slots 52 and 54 are drawn over cam pin 22 such that the jaws 12 and 14 open or close.

Figure 7:
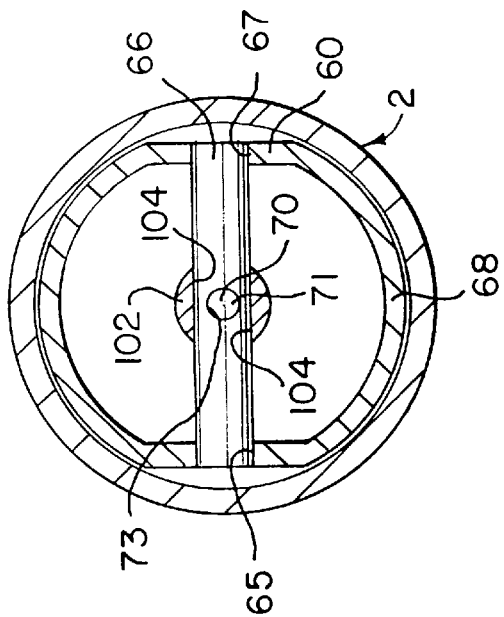
FIG. 7 is a sectional view of the jaw assembly depicted in FIGS. 1, 2, 3, 4, 5 and 6, taken along line 7—7 in FIG. 5.
Figure 8:
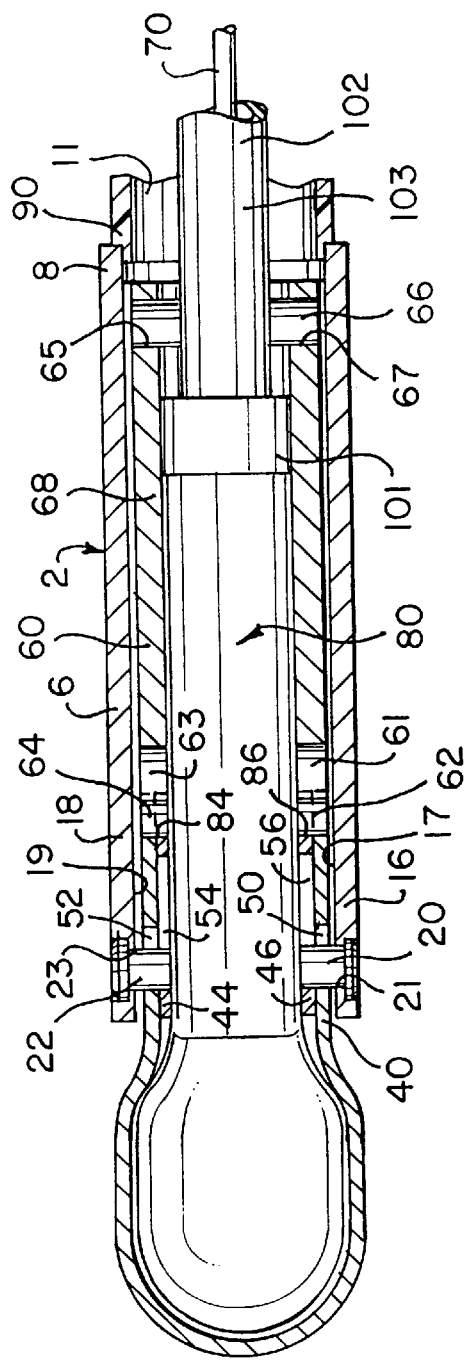
FIG. 8 is a sectional view from above of the jaw assembly depicted in FIGS. 1, 2, 3, 4, 5, 6 and 7, taken along line 8—8 in FIG. 5.

Axial movement of the jaw shanks 40, 42, 44, 46 relative to the jaw housing 2 is provided by the puller member 60 which is supported within jaw assembly housing 2 such that it is slidable along the longitudinal axis of the device. In the embodiment shown in FIGS. 2–10, the puller number 60 is configured to fit closely within the cross-sectional profile of the lumen of the jaw housing 2 so that the volume of that portion of the tissue sample storage area 80 within the housing 2 is maximized. The puller member 60 has a tube-like body 68 defining a lumen which comprises a portion of the tissue sample storage area 80. A proximal end of the body 68 of the puller member is connected to a distal end 71 of a drive wire 70 by, for example, a puller pin 66, or other means for connection. Alternatively, the drive wire 70 can be connected directly to the body 68 by, for example, fastening the distal end 71 of the drive wire to a surface of the body 68, or to a bore in the body 68. In this case, the distal end 71 of the drive wire 70 could preferably be bent at an angle to the longitudinal axis of the device to facilitate attachment to the body 68. When a puller pin 66 is used, opposite ends of the puller pin 66 are fastened to bores 65, 67, respectively, (FIGS. 7 and 8) in the body 68 of puller member 60. Similarly, the end 71 of drive wire 70 is, for example, welded or swaged to into a bore 73 in the center portion of the puller pin 66 (FIGS. 7 and 8). It will be understood that the drive wire 70 should be dimensioned and made of a material suitable to transmit from the handle assembly to the jaw assembly sufficient force to close the jaws on a portion of a tissue mass and to thereby sever a tissue sample from the tissue mass.

At a distal end of puller member 60, puller pivots 62, 64 are formed on the end of pivot supports 61, 63, respectively. Each pivot 62, 64 on its respective support 61, 63 extends distally along the longitudinal axis of the device from an opposite side of the puller member body 68. The pivot 62 and its support 61 is preferably in linear alignment along the longitudinal axis with jaw shank 40 of upper jaw 12 and jaw shank 46 of lower jaw 14. Similarly, the pivot 64 and its support 63 is preferably in linear alignment along the longitudinal axis with jaw shank 42 of upper jaw 12 and jaw shank 44 of lower jaw 14. By aligning the pivots and the jaw shanks linearly along the longitudinal axis, the volume of the tissue sample storage area 80 within the jaw assembly is maximized, and interference of the puller member with the movement of tissue samples 82 into and out of the tissue sample storage area 80 is avoided.

The drive wire 70 is coaxially positioned in the tubular shaft 11 and is movable along the longitudinal axis and relative to the shaft 11. The drive wire 70 extends from the distal end 71 connected to the puller member 60 in housing 2 through the tubular shaft 11 to a proximal end 69 which is connected to the finger member 25 on the handle assembly 7. The distal end 90 of the tubular shaft 11 is fixedly mounted to the proximal end 8 of the housing 2 by an adhesive, by welding, by swaging, or by other methods known in the art. The proximal end 92 of the tubular shaft 11 is fixedly mounted to the thumb member 27 by an adhesive by welding, by swaging or by other well known means. Thumb ring 26 is preferably integrally formed on thumb member 27. Finger member 25 is slidably supported on thumb member 27, for example, by way of a bore 29 in finger member 25 through which thumb member 27 passes (FIGS. 1B–1C). Rotation about the longitudinal axis of the finger member 25 relative to the thumb member 27 is prevented by, for example, providing the thumb member 27 and the bore 29 with complementary cross-sectional shapes. While rotation about the longitudinal axis restrained, sufficient movement of the finger member 25 relative to the thumb member 27 along the longitudinal axis, i.e., axial movement, is provided to permit the operation of the jaws. The finger rings 24 are integrally molded as part of finger member 25. Accordingly, axial movement of the finger rings 24 relative to the thumb ring 26 provides corresponding movement of the drive wire 70 relative to the tubular shaft 11, which in turn provides corresponding movement of the puller member 60 relative to the jaw housing 2. Axial movement of the puller member 60 relative to the housing 2 is translated into pivotal movement of the jaws 12, 14 by the cam pins 22, 20 sliding in the cam slots 50, 52, 54, 56.

The drive wire 70 may be connected to the finger member 25 by any known means. For example, the proximal end 69 of the drive wire 70 extends from within the proximal end of the drive shaft 102 to be attached to a cross member 112. The cross member 112 is positioned perpendicular to the longitudinal axis of the device 5 and connects opposite side walls of the bore 29 in the finger member 27. The cross member 112 has a threaded bore 115 along the longitudinal axis of the biopsy device 5. The cross member 112 has a wire bore 114 along the longitudinal axis of the biopsy devices. The threaded bore 115 and the wire bore 114 intersect. The proximal end 69 of drive wire 70 passes through the wire bore 114 in the cross member 112. A set screw 116 in threaded bore 115 is tightened to engage the end 69 of the drive wire 70 in the wire bore 114 at the point where the threaded bore 115 and wire bore 114 intersect. It will be understood that numerous other attachment arrangements may be substituted for the foregoing construction.

The jaw assembly is provided with a tissue ejector 101 (FIGS. 4, 6, 8, 9, 10) in the form of a plunger sized to closely fit the cross-sectional dimensions of the tissue sample storage area 80 in the jaw assembly, i.e., in the puller member 60 and between the jaw shanks. The tissue ejector 101 is slidable in the tissue sample storage area 80 along the longitudinal axis of the device 5 in response to movement of the slidable ejector knob 28 projecting from the handle assembly 7 (FIGS. 1, 1A). The ejector 101 is connected to the ejector knob 29 by a drive shaft 102 which is supported in the flexible tubular shaft 11 of the device 5. Preferably, the drive shaft 102 is tubular, is coaxially supported in the tubular shaft 11, and in turn coaxially supports the drive wire 70 of the puller member 60. The distal end 103 of the drive shaft 102 is connected directly to the ejector by welding, swaging or other known means.

At the handle assembly, the proximal end 109 of the drive shaft 102 is connected to the ejector knob 28 by way of a member 105 slidably supported within the body of the thumb member 27. The proximal end 109 of the drive shaft 102 is fixedly connected to a bore 108 in a distal end 106 of the member 105 by, for example, welding, adhering or attaching by other known means. A proximal end 108 of the member 105 has a distally directed surface 110. An ejector spring 107 is provided between the distally directed surface 110 of the member 105 and the cross member 112, which connects opposite side walls of bore 29 in finger member 25. The spring 107 is provided to bias the member 105 rearwardly, and thus to correspondingly bias the ejector 101 to a proximal position in the jaw assembly, as shown in FIG. 5. The member 105 is provided with a clearance 111 dimensioned to clear shaft 112, such that the member 105 is freely movable relative to the cross member 112. Accordingly, sliding movement of the ejector knob 28 relative to the thumb member 27 provides a corresponding movement.

A distal end 103 of the drive shaft 102 is provided with at least one lateral opening in the form of a longitudinally extending lateral slot 104. The slot 104 is provided to permit the drive wire 70 to be connected to the puller member 60. In an embodiment in which the drive wire is connected directly to the puller member by, for example, bending a portion of the distal end 71 of the drive wire 70 at a right angle to the longitudinal axis (not shown), a single lateral slot 104 will accommodate the connection of the drive wire 70 to the puller member 60. In the embodiment having a puller pin 66 connecting the drive wire 70 to the puller member 60 (shown in FIGS. 5 and 7–10), the distal end 103 of the drive shaft 102 is provided with opposite lateral slots 104 sized to permit passage of the puller pin 66 from its connection to the drive wire 70, i.e., at the central axis of the shaft 11, radially outwardly through the opposite slots 104 in the drive shaft 102 to bores 65 and 67 in opposite sides of the puller member body 68. The slot or slots 104 are dimensioned sufficiently long enough to permit the drive shaft 102 and drive wire 70 to be movable freely and independently of each other, and to permit the drive shaft 102 and drive wire 70 to be movable freely and independently of the shaft 11. In this way, the ejector 101 and the pair of jaws 10 are operable independently of each other, and independently of the jaw housing 2.

The operation of the preferred embodiment depicted in FIGS. 1A–10 will now be described. With the pair of jaws 10 closed as shown in FIG. 3, the distal end 9 of the biopsy device 5 is inserted into a body cavity of a patient through an endoscope (not shown). After the jaws 10 are adjacent to a target tissue mass 81 (FIG. 9), the operator manipulates the handle assembly to open the jaws 10. This is done by moving the finger rings 24 relative to the thumb ring 26. At this point in the operation, the ejector knob 28 and member 105 is rearwardly (proximally) biased by the spring 107, which in turn holds the ejector 101 in a proximal-most position in the jaw assembly such that the tissue sample storage area 80 is at its maximum volume (FIG. 5). The distal end 9 of the biopsy device is then advanced to engage a portion of the tissue mass 81 to be sampled, the handle assembly is again manipulated to closed the jaws, and a tissue sample 82 is severed from the tissue mass 81. If a second tissue sample is desired, the foregoing operation is repeated. Each successive tissue sample 82 collected in the jaw assembly pushes the previously collected tissue sample into the tissue sample storage area 80. The sample collecting operation is repeated until the operator has retrieved a desired number of samples less than the maximum capacity of the tissue sample storage area 80, or until the maximum capacity of the tissue sample storage area 80 is achieved (approximately 6–10 samples). Then, with the jaws closed, the distal end 9 of the biopsy device is withdrawn from the patient. Once the distal end 9 of the biopsy device has been withdrawn from the patient, the thumb ring and finger rings are again manipulated by the operator to open the jaws, and the samples are collected from the tissue sample storage area 80 through the open jaws. Collection of the tissue samples 82 from the tissue sample storage area 80 through the jaws is facilitate by manipulation of the ejector knob 28 against the urging of spring 107 to advance the ejector 101 from within the jaw housing towards the jaws (FIG. 10). The tissue samples 82 are pushed out of the jaw assembly ahead of the ejector 101, and collected by the operator in a suitable receptacle (not shown). After collection of the tissue samples 82 from the jaw assembly, the jaws can be closed, and the distal end 109 of the biopsy device can then be re-inserted in the patient to collect more samples if desired.

An alternative embodiment of a jaw assembly according to the present invention is shown in FIGS. 11–14. This jaw assembly is secured to a shaft 11 which is in turn secured to a handle assembly (not shown) similar to the handle assembly described above. The alternative embodiment of the jaw assembly comprises a pair of jaws 210 pivotally mounted on a base member 202. The base member 202 is secured to the distal end 90 of the elongate flexible shaft 11 by conventional means. A drive wire 70 coaxially positioned in the shaft 11 has a distal end 71 which extends from the distal end 90 of the shaft 11 through a lumen 299 in the base 202 to a point between the arms 216, 218. The pair of jaws 210, comprising an upper jaw 212 and a lower jaw 214 are supported on pair of arms 216 and 218 extending from the base 202. Each jaw has a semi-cup shaped distal end 230, 232 respectively, comprised of opposite sidewalls 260, 262, 264, 266, an end wall 261, 263, and a lateral wall 265, 267. Each cup has a sharpened edge 234, 236 along the edge of the end wall and continuing along a part of the sidewalls. The sharpened edge 234, 236 is adapted for cutting tissue from a tissue mass. The dimensions of the distal end of each jaw together with the length of the sharpened edges 234, 236 along the longitudinal axis of the biopsy device define the cutting or "biting" portion of the pair of jaws. The dimensions of the biting portion of the pair of jaws substantially determines the maximum size of each tissue sample taken. The dimensions of the distal end of each jaw and the length of the sharpened edges can thus be selected to facilitate the taking of samples of a particular size.

The upper jaw 212 has a shank 240 extending proximally from the cup shaped portion of the jaw towards the base 202 of the jaw assembly. The shank 240 is laterally offset from the longitudinal axis of the biopsy device. The shank 240 has a length and a width defining an outwardly directed planar surface 241 which faces and is aligned with an inwardly directed planar surface 217 (FIG. 14) on arm 216. The width of the shank 240 is preferably greater than a radius of the pair of jaws 210, such that the outwardly directed planar surface 217 is broad relative to the dimensions of the jaw assembly. Interaction of the outwardly directed planar surface 241 and the inwardly directed planar surface 217 serves to maintain the alignment of the jaw 212 relative to the jaw assembly, and in particular, relative to the jaw 214. A cam slot 250 is provided in the shank 240. The cam slot is positioned at a first diagonal relative to the longitudinal axis of the biopsy device 5. A cam pin 220 is secured to and extends inwardly from the arm 216. The portion of the cam pin 220 extending from arm 216 is sized to slidably engage the cam slot 250, and is captured in the cam slot 250 by, for example, an expanded inner end 221 of the cam pin 220.

The lower jaw 214 has a shank 244 extending proximally from the cup shaped portion of the jaw towards the base 202 of the jaw assembly. The shank 244 is laterally offset from the longitudinal axis of the biopsy device, preferably in a direction opposite the lateral offset of the shank 240 of the upper jaw 212, so that the shank 244 is adjacent the arm 218. The shank 244 has a length and a width defining an outwardly directed planar surface 245 (FIG. 14) which faces and is aligned with an inwardly directed planar surface 219 (FIGS. 11–14) on arm 218. The width of the shank 244 is preferably greater than a radius of the pair of jaws 210, such that the outwardly directed planar surface 219 is broad relative to the dimensions of the jaw assembly. Interaction of the outwardly directed planar surface 245 and the inwardly directed planar surface 219 serves to maintain the alignment of the jaw 214 relative to the jaw assembly, and in particular, relative to the jaw 212. A cam slot 254 is provided in the shank 244. The cam slot is positioned at a second diagonal relative to the longitudinal axis of the biopsy device 5. A cam pin 222 is secured to and extends inwardly from the arm 218 along a common axis with cam pin 220. The portion of the cam pin 222 extending from arm 218 is sized to slidably engage the cam slot 254, and is captured in the cam slot 254 by, for example, an expanded inner end 223 of the cam pin 222. Each cam pin 220, 222 may be integrally formed with the respective arm 216, 218, or may be a separate component which is secured by known means to a surface of the respective arm, or as shown in FIGS. 11–14, in a bore in the respective arm.

Because the shank 240 of jaw 212 and the shank 244 of jaw 214 are laterally offset to opposite sides of the longitudinal axis of the biopsy device, a relatively large volume of unoccupied space is defined behind the biting portion of the pair of jaws, between the opposite lateral walls 265 and 267 of the jaws 212 and 214. This unoccupied space comprises the tissue sample storage space 280 of this embodiment of the jaw assembly, wherein approximately four to six tissue samples can be collected. A slot 270, 272, also known as a fenestration, is provided in each lateral wall 265, 267 and is oriented along the longitudinal axis of the device. The fenestration 270, 272 serves two purposes. First, the fenestration 270, 272 permits fluids to drain from collected samples (not shown). Second, the fenestration 270, 272 tends to grip each tissue sample, a portion of which is squeezed into the fenestration when the jaws are closed to sever the sample from a tissue mass. As successive samples are collected in the tissue sample storage area 280, previously collected samples are pushed deeper into the sample storage area 280. The successively collected samples are indexed along the fenestration in the order that they are collected, facilitating later analysis, and the samples are retained with sufficient force to prevent premature loss of individual samples from the jaw assembly. Each fenestration 270, 272 in this particular embodiment is slightly tapered such that the fenestration is narrower toward the distal end of the jaw, and wider toward the proximal end of the jaw. This slight taper is provided to facilitate the sliding movement of tissue samples deeper into the tissue sample storage area 280 as successive tissue samples are collected. Because tissue samples tend to jam in an un-tapered fenestration, i.e., sliding movement deeper into a storage area is hampered, the slight taper is essential for this particular configuration to permit the collection of multiple samples. This embodiment is not shown with an ejector means, although an ejector means similar to that described above maybe provided. When sufficient samples have been collected in the jaw assembly of this embodiment, the jaw assembly end of the device is withdrawn from the patient, and the samples are removed from the opened jaws by tapping the jaw assembly, or by scraping the samples from the jaw assembly.

The drive wire 70 is operatively connected to each of the jaw shanks 240, 244 by a puller member 259. In the preferred embodiment shown in FIGS. 11–14, the puller member 259 is rod shaped, but the member may have any suitable shape. The puller member 259 is positioned perpendicular to the longitudinal axis, such that the longitudinal axis of the device intersects it at a midpoint. The drive wire 70 is attached to the puller member 259 by, for example, securing the end 71 of the drive wire in a bore 271 in the puller member 259. Opposite ends of the puller member 259 extend radially outwardly to attach to each jaw shank 240, 244. Each end of the puller member is attached to a jaw shank 240, 244 by securing the end in a bore 257, 255 in the respective shank. In response to movement of the drive wire 70 along the longitudinal axis relative to the shaft 11, the puller member 259 secured to the drive wire 70 moves relative to the base 202 secured to the shaft 11. Longitudinal movement of the puller member 259 relative to the base 202 moves the jaw shanks 240, 244 relative to the base 202, and therefore, relative to the arms 216, 218 and cam pins 220, 220 secured relative to the base. Longitudinal movement of the jaw shanks 240, 244 relative to the base 202 thus causes the cam slots 250, 254, which are oriented at opposite diagonal angles relative to the longitudinal axis, to slide over the cam pins 220, 222. The sliding of the opposite diagonal slots on the cam pins translates longitudinal movement into the lateral movement to open and close the jaws.

Figure 15:
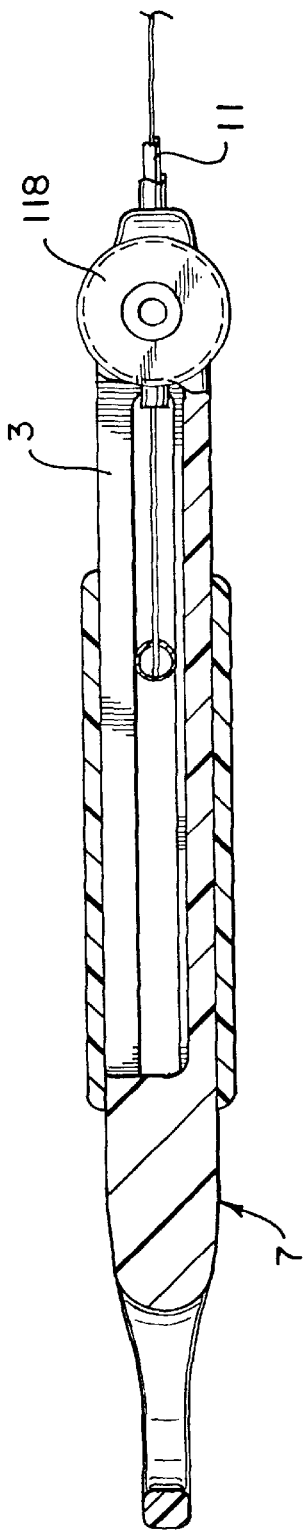
FIG. 15 is a sectional view from the side of an alternative embodiment of the handle assembly depicted in FIG. 1, showing a tissue collection chamber.
Figure 16:
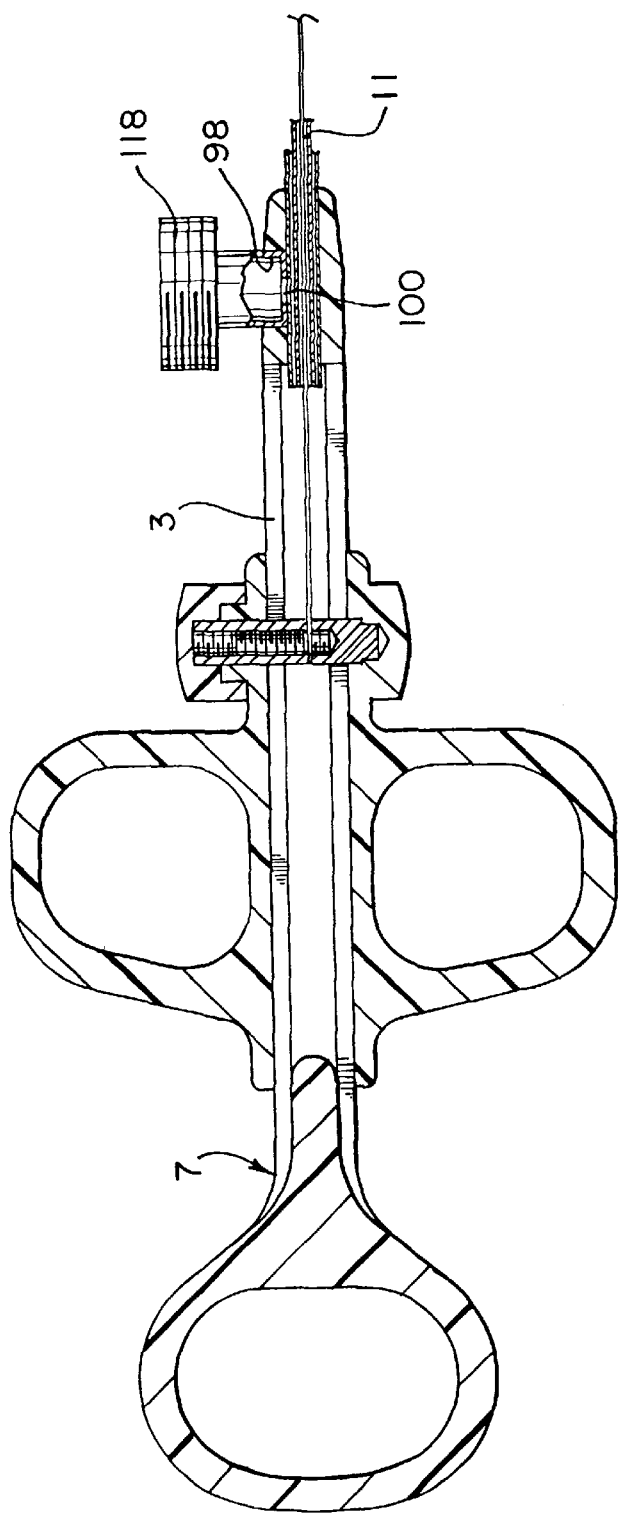
FIG. 16 is a sectional view from the top of the alternative embodiment of the handle assembly depicted in FIGS. 1 and 15, showing a top plan view of the tissue collection chamber.

An alternative embodiment of the proximal end 3 of the biopsy device 5 is shown in FIG. 15. In this alternative embodiment, the proximal end 3 of the biopsy device 5 is provided with a vacuum means through a connection 118 that is in fluid communication with a lumen connected to the tissue sample storage area 80 in the jaw assembly. The lumen connecting the vacuum means to the tissue sample storage area 80 is preferably the lumen in shaft 11. The connection 118 is for attaching suction means, e.g., a vacuum, to the device 5 to retrieve tissue samples 82 from the jaw assembly through the lumen without withdrawing the device 5 from the patient. The vacuum may be provided, for example, from a remote source through a tube (not shown) which is secured to the connection 118 by conventional means. In this alternative embodiment, there is no need for a tissue ejector or tissue ejector drive shaft. Thus, the jaw assembly and the lumen of tubular shaft 11 have more unoccupied volume that can accommodate the movement of tissue samples 82 from the biting portion of the jaws to the handle assembly 7 under vacuum pressure. And the handle assembly is simplified because it does not have the ejector related components, e.g., the ejector knob, supporting member and spring. In this alternative embodiment, the handle assembly 7 includes a tissue collection chamber 98 which is in fluid communication with the lumen of tubular shaft 11 by way of a passage 100. When a vacuum is applied to the chamber 98 from an external source (not shown) via connection means 118, tissue samples 82 are drawn from the jaw assembly, e.g., from the tissue sample storage area 80, through the shaft 11 into the chamber 98 by way of the passage 100. By using suction means to withdraw tissue samples from the jaw assembly, an unlimited number of samples can be collected without withdrawing the biopsy device from the patient.

The foregoing arrangement provides several advantages. The rearwardly open ended sample storage portion of the jaws and sample storage area in the housing permits the collection of multiple tissue samples. The housing, and the jaws mounted to the housing, can be held axially stationary relative to the endoscopic member, and thus, relative to the sampling site, so that tissue sampling is more precise and better samples can be obtained, e.g., the jaws do not "pull away" from a sample site. Since all of the moving parts of the jaw assembly, except the jaws, are contained within the housing, the jaws can be operated without disturbing surrounding tissue, further enhancing tissue sampling precision. Furthermore, the parts of the jaw assembly are arranged to create a maximum amount of tissue sample storage space in the assembly by locating them as close as possible to the outer dimensions of the jaw assembly. A final advantage of the present construction is realized by way of the diagonally oriented slots on jaw shanks wider than the cross-sectional radius of the jaw assembly, which provides a jaw actuating mechanism that occupies minimum space, yet provides significant mechanical advantage in actuating the jaws.

It will be understood that the foregoing description of the invention is intended merely to be illustrative thereof and that other modifications and embodiments may be apparent to those skilled in the art without departing from the spirit of the invention.

What is claimed is:

1. An endoscopic biopsy device having a proximal end and a distal end defining a longitudinal axis, the distal end of which is adapted for obtaining from a tissue mass in a body cavity a plurality of tissue samples without withdrawing the distal end from the cavity, the device comprising:

an elongate flexible tubular shaft having a proximal end and a distal end;

a drive wire having a proximal end and a distal end, the drive wire slidably supported in the shaft; and a jaw assembly mounted to the distal end of the shaft in a longitudinally fixed position with respect to the shaft, the jaw assembly comprising:

a housing having a proximal end and a distal end, the proximal end of the housing attached to the distal end of the shaft;

a puller member positioned inside the housing and attached to the distal end of the drive wire;

a pair of jaws, a distal end of each of the jaws extending from the housing and adapted to cut a portion of tissue from the tissue mass, a first shank extending from a proximal end of each of the jaws, the first shank of each jaw laterally offset from and in alignment with the longitudinal axis of the device, the first shank of each jaw extending into the distal end of the housing, the first shank of each jaw supporting cam means and pivot means, the first shank of each jaw connected to the distal end of the housing by one of the cam means and the pivot means, and connected to the puller member by the other of the cam means and the pivot means, whereby longitudinal movement of the drive wire relative to the shaft causes the pair of jaws to open and close; and a tissue sample storage area adapted to receive the plurality of tissue samples, at least a portion of the tissue sample storage area defined by the first shank of each jaw being offset from the longitudinal axis;

wherein the pair of jaws is the only jaw assembly element movable relative to the shaft that is exposed externally of the biopsy device.

2. The endoscopic biopsy device of claim 1 wherein the distal end of the housing further comprises an inwardly directed first planar surface, the first shank of each jaw further comprises an outwardly directed planar surface and the outwardly directed planar surface of one of the pair of jaws is in planar alignment with the first planar surface.

3. The endoscopic biopsy device of claim 2 wherein the distal end of the housing further comprises an inwardly directed second planar surface, and the outwardly directed planar surface of the other of the pair jaws is in planar alignment with the second planar surface.

4. The endoscopic biopsy device of claim 2 wherein each jaw further comprises a second shank extending from an opposite side of the proximal end of each jaw, the second shank of each jaw laterally offset to a side of the longitudinal axis opposite the first shank, the second shank of each jaw extending into the distal end of the housing, the second shank of each jaw supporting cam means and pivot means, the second shank of each jaw connected to the distal end of the housing by one of the cam means and the pivot means, and connected to the puller member by the other of the cam means and the pivot means, the second shank of each jaw having an outwardly directed planar surface; the distal end of the housing further comprises an inwardly directed second planar surface; the planar surface of the first shank of each jaw is in planar alignment with the first planar surface, and the planar surface of the second shank of each jaw is in planar alignment with the second planar surface.

5. An endoscopic biopsy device having a proximal end and a distal end defining a longitudinal axis, the distal end adapted for obtaining from a mass of tissue in a body cavity a plurality of tissue samples without withdrawing the distal end from the cavity, the device comprising:

an elongate flexible tubular shaft defining a shaft lumen, the shaft having a proximal end and a distal end;

a drive wire extending axially through the shaft lumen, the drive wire having a proximal end and a distal end, the drive wire axially movable relative to the shaft;

a biopsy jaw assembly including:

a housing having a base with a proximal end and a distal end, the proximal end of the base mounted to the distal end of the shaft in a fixed position with respect to the distal end of the shaft, the base having a housing lumen aligned and in communication with the shaft lumen, a pair of arms integrally formed on and extending longitudinally from the distal end of the base, each of the pair of arms positioned on an opposite side of the distal end of the base, each of the pair of arms having an inwardly directed planar jaw interface surface facing the jaw interface surface of the other of the pair of arms, the housing having an outer width taken along a radial axis;

a puller member connected to the distal end of the drive wire, said puller member positioned within and longitudinally movable in said housing; and a pair of jaws having a width, each jaw having a semi-cup shaped distal end with a depth, and each jaw having a sharpened edge with a length along the longitudinal axis, the pair of jaws having a biting portion defined by the width of the pair of jaws, by the combined depth of the distal end of each jaw, and by the length along the longitudinal axis of the sharpened edge, a first shank extending from a proximal end of each jaw, the first shank of each jaw extending between the pair of arms, the first shank of each jaw having a length and a width defining an outwardly directed planar surface in planar alignment with the jaw interface surface of one of the pair of arms, the width of the first shank is greater than one half of the outer width of the housing, the first shank of each jaw is laterally offset from the longitudinal axis of the biopsy device;

a cam slot and a cam pin connecting the first shank of each jaw to one of the puller member and one of the pair of arms;

a pivot pin and a bore connecting the first shank of each jaw to the other of the puller member and one of the pair of arms; and a tissue sample storage area defined between the biting portion and the puller member;

wherein the upper biopsy jaw and the lower biopsy jaw are the only jaw assembly elements movable relative to the shaft that are exposed externally of the biopsy device.

6. The endoscopic biopsy device of claim 1 wherein a second portion of the tissue sample storage area is defined by a portion of the housing lumen.

7. The endoscopic biopsy device of claim 1 further comprising:

an ejector including a distally facing wall positioned in the jaw assembly housing, the wall dimensioned to define a proximal end of the tissue storage area, and a drive member, the ejector movable along the longitudinal axis in response to movement of the drive member such that the wall is repositionable from the proximal end of the housing to the distal end of the housing to eject tissue samples.

8. The endoscopic biopsy device of claim 7 wherein a portion of the drive member is tubular.

9. The endoscopic biopsy device of claim 8 wherein the distal end of the drive wire extends into the tubular portion of the drive member, and the tubular portion of the drive member further comprises a lateral slot, the puller is connected to the distal end of the drive wire through the slot and the slot is dimensioned to permit the jaws to be operated independently from the ejector.

10. The endoscopic biopsy device of claim 5 wherein at least one of said pair of jaws further comprises a lateral wall having a fenestration oriented along the longitudinal axis.

11. The endoscopic biopsy device of claim 10 wherein said fenestration has a first width at a proximal end, and a second width at a distal end, and the first width is greater than the second width.

* * * * *